United States Patent
Jacquemet et al.

(10) Patent No.: US 9,228,087 B2
(45) Date of Patent: Jan. 5, 2016

(54) METHOD OF MANUFACTURE OF AQUEOUS SUSPENSIONS OF TALC FROM AN ACRYLIC POLYMER WITH A GRAFTED SURFACTANT GROUP, SUSPENSIONS OBTAINED AND THEIR USES

(71) Applicant: COATEX S.A.S., Genay (FR)

(72) Inventors: Christian Jacquemet, Lyons (FR); Jean-Marc Suau, Lucenay (FR)

(73) Assignee: COATEX, Genay (FR)

( * ) Notice: Subject to any disclaimer, the term of this patent is extended or adjusted under 35 U.S.C. 154(b) by 0 days.

(21) Appl. No.: 13/652,537

(22) Filed: Oct. 16, 2012

(65) Prior Publication Data

US 2013/0109760 A1    May 2, 2013

Related U.S. Application Data

(60) Provisional application No. 61/551,947, filed on Oct. 27, 2011.

(30) Foreign Application Priority Data

Oct. 26, 2011   (FR) ...................... 11 59694

(51) Int. Cl.
| A61K 9/14 | (2006.01) |
| C09C 1/28 | (2006.01) |
| D21H 19/40 | (2006.01) |
| D21H 19/58 | (2006.01) |
| B01F 17/00 | (2006.01) |
| A61K 9/16 | (2006.01) |

(52) U.S. Cl.
CPC .............. *C09C 1/28* (2013.01); *B01F 17/0007* (2013.01); *B01F 17/0028* (2013.01); *D21H 19/40* (2013.01); *D21H 19/58* (2013.01); *A61K 9/1694* (2013.01); *C01P 2006/12* (2013.01); *C01P 2006/22* (2013.01)

(58) Field of Classification Search
None
See application file for complete search history.

(56) References Cited

U.S. PATENT DOCUMENTS

| 6,093,764 | A | 7/2000 | Egraz et al. |
| 6,946,510 | B2 | 9/2005 | Suau et al. |
| 2004/0019148 | A1 * | 1/2004 | Suau et al. ..................... 524/556 |
| 2005/0143511 | A1 * | 6/2005 | Suau et al. ..................... 524/425 |
| 2009/0308553 | A1 * | 12/2009 | Souzy et al. ............... 162/164.5 |
| 2010/0076139 | A1 | 3/2010 | Mongoin et al. |
| 2012/0053280 | A1 | 3/2012 | Mongoin et al. |

FOREIGN PATENT DOCUMENTS

| EP | 0 892 020 | 1/1999 |
| FR | 2 900 410 | 11/2007 |
| FR | 2900410 A1 * | 11/2007 |
| FR | 2 913 426 | 9/2008 |

OTHER PUBLICATIONS

International Search Report issued by the European Patent Office on Nov. 27, 2012, in corresponding PCT application PCT/FR2012/052277.

* cited by examiner

*Primary Examiner* — Susan Tran
(74) *Attorney, Agent, or Firm* — Oblon, McClelland, Maier & Neustadt, L.L.P.

(57) ABSTRACT

A method of manufacture of an aqueous suspension of talc, using a copolymer of (meth)acrylic acid with an oxyalkylated monomer with a surfactant group, an aqueous suspension of talc which may be obtained by such a method, and the use of these suspensions in various applications.

15 Claims, No Drawings

METHOD OF MANUFACTURE OF AQUEOUS SUSPENSIONS OF TALC FROM AN ACRYLIC POLYMER WITH A GRAFTED SURFACTANT GROUP, SUSPENSIONS OBTAINED AND THEIR USES

REFERENCE TO PRIOR APPLICATIONS

This application claims priority to U.S. provisional application Ser. No. 61/551,947, filed Oct. 27, 2011; and to French patent application 11 59694, filed Oct. 26, 2011, both incorporated herein by reference.

FIELD OF THE INVENTION

The present invention relates to a new method for suspending talc in water, using a polymeric additive enabling aqueous suspensions of talc to be manufactured having an as-yet unequalled compromise between a high dry extract, improved stability and a smaller dose of dispersant. This result is particularly advantageous since the many applications of aqueous suspensions of talc, and the difficulty of suspending this particularly hydrophobic mineral in water, are known. Additional objects, advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. In this regard, the description herein is to be understood as illustrative in nature, and not as restrictive.

BACKGROUND OF THE INVENTION

Talc is a mineral used in many applications. In the paper manufacturing industry it is used notably as a filler, but can also be used in paper coatings, or as an additive enabling the quantity of adhesives (pitch or stickies) in the paper manufacturing method to be reduced; it is also used in paints, plastics and filled rubbers, in ceramics, within food and cosmetic formulations and even in agriculture.

Talc can be transported in the form of powder, but it is also suspended in water for reasons relating to ease of transport, unloading and decanting of a liquid product, compared to a powder product. In addition, fine powders also represent a danger for human beings, if inhaled in too large a quantity. The suspension of the talc may be preceded by a step of granulation, by agglomerating individual talc particles in order to form a wet granulate.

However, talc is a highly hydrophobic substance, having surface energy on the order of 68 to 70 $J/cm^2$. Consequently, suspending a substantial quantity of this mineral material in water without however reaching levels of viscosity which would make the suspension unfit for storage or for handling represents a technical challenge for the skilled man in the art. This is reported in "The importance of surface energy in the dispersion behaviour of talc particles in aqueous media" (Powder Technology, 2009, 190 (1-2), pp. 242-246).

The twin problem is therefore faced of increasing what is called the dry extract (or % by dry weight of talc present in the aqueous suspension) of the aqueous talc suspension, whilst giving the latter a rheology compatible with its use (i.e. by limiting the increase of viscosity of the suspension). This latter viscosity may be measured using any technique familiar to the skilled man in the art, such as a Brookfield™ rheometer, a device of the Ford™ cup type, etc.

The choice of the measurement and of the associated device is of little importance, provided they enable the rheological properties of the suspension during storage and/or handling to be apprehended. This independence is recalled in document EP 1 074 293 A1, which covers in very general fashion the dispersal of mineral matters in water, talc being notably mentioned among the substances to be dispersed.

To resolve the problem mentioned above, it is well known to use dispersing agents, which are introduced during the step of suspension of the talc in water, and/or during the step, if applicable, of granulation preceding it.

The skilled man in the art is familiar, on this subject, with document JP 63-175197 which recommends the use of acrylic polymers in a blend with polylakylene glycol esters. A suspension of a dry extract of around 60% is obtained; its rheological properties are studied by means of a sieving test; easy and rapid flow of the suspension is observed for a sieve mesh equal to 150 µm. However, the dose of dry dispersant used is at around 10% by weight relative to the dry weight of talc: the specifications must therefore be put into perspective with regard to this high quantity of dispersant.

Similarly, document JP 02-253836 recommends the use of a (meth)acrylic copolymer in combination with a sulphosuccinic acid. Even if a dry extract of 65% for a Brookfield™ viscosity at 100 revolutions per minute is accomplished of between 300 and 680 mPa·s is obtained, the proportion of dispersant of between 2 and 3% by dry weight relative to the dry weight of talc cannot satisfy the skilled man in the art.

Document FR 2 380 065 A1 is also known, which describes aqueous suspensions of talc having dry extracts of over 65%, and Brookfield™ viscosities at 100 revolutions per minute of the order of 1,000 mPa·s. However, the examples demonstrate that the quantity of dry weight of dispersant must be higher than 1% of the dry weight of talc, and preferentially of the order of 3%. Finally, the dispersant used is a phenol salt, and more specifically a phenol alkyl. And these substances are now prohibited in industry, notably in water-based paints, which constitute one of the potential applications of aqueous suspensions of talc.

Documents U.S. Pat. No. 6,267,811 A1 and WO 2010 055191 A1 are also known, which recommend implementing a CMC (carboxymethyl cellulose)/sodium polyacrylate system. However, the level of performance attained by this pair is modest, in respect of the rheology of the suspension given its dry extract. In addition, this solution has the disadvantage that it uses two components, which increases commensurately the storage and decanting installations (the modified cellulose in this case acts as a wetting agent).

A variant of the previous solution lies in the use of a sodium polyacrylate with a surfactant (GB 2 019 822). Although the characteristics of the resulting aqueous suspension of talc in the sense the present invention are improved, the formation of a very abundant foam is then observed, which is a very prejudicial factor for the final application, since the foam results from the presence of the surfactant in free form in the water. Both the polyacrylate/CMC and polyacrylate/surfactant technical solutions were, incidentally, subjected to comparative testing in the present application.

Currently, it is still the technical solution provided in document EP 0 892 020 A1, which is however more than 10 years old, which provides the best compromise between viscosity/dry extract specifications and low rates of dispersant, without producing a foam. This solution is based on the use of a hydrosoluble copolymer, consisting of a first carboxylic monomer (and notably a (meth)acrylic one) and of a second monomer carrying a grafted surfactant group, where the copolymer satisfies the following formula:

R—(OE)$_m$-(OP)$_n$—R' where
- m and n designate integers of less than or equal to 100, at least one of which is non-zero,
- OE and OP designate respectively ethylene oxide and propylene oxide,
- R designates a polymerisable group, and preferentially the methacrylate or methacrylurethane group,
- R' designates a linear or branched alkyl, alkylaryl, arylalkyl, aryl group having at least 22 carbon atoms or a dialkylamine having at least 22 carbon atoms.

The many examples in this disclosure demonstrate that it is possible to manufacture, with only 1% by dry weight relative to the dry weight of talc of the copolymers described above, aqueous suspensions which have a dry talc extract close to 65% of their weight, and which are at once stable, handleable and compatible with their end uses. The best results are obtained by choosing an aryl group having 30 carbon atoms.

SUMMARY OF THE INVENTION

The inventors, who have pursued their research efforts with a view to improving the dry extract/viscosity compromise of an aqueous talc suspension, and of limiting the quantity of dispersant used, have now achieved a solution which goes beyond the specifications described in document EP 0 892 020 A1. This solution is particularly original since it is based on a copolymer of (meth)acrylic acid with a monomer of formula similar to the one described in document EP 0 892 020 A1, but having a major difference in respect of the choice of R': in the present invention this is hydrogen or a terminal linear or branched alkyl group having fewer than 14 carbon atoms.

This latter monomer is therefore much less hydrophobic than its predecessor mentioned in document EP 0 892 020 A1; its surfactant character is for its part very much reduced. The solution developed by the inventors is therefore particularly surprising in that it is opposed to a teaching more than ten years old, and related in the abovementioned document, which recommended a (meth)acrylic copolymer with a very strongly surfactant monomer (having a terminal group having at least 22 carbon atoms) to disperse the talc efficiently in the water.

It is clearly shown herein, on the basis of a viscosity measurement of the Ford™ cup type, that aqueous suspensions of talc having a dry extract of over 60% have, in the context of the invention, a viscosity lower than those manufactured:
- according to document EP 0 892 020 A1 (a surfactant monomer having more than 22 carbon atoms);
- according to documents U.S. Pat. No. 6,267,811 A1 and WO 2010 055191 A1 (polyacrylate/CMC pair);
- and do not lead to the formation of foam, unlike the solution recommended in document GB 2 019 822 (polyacrylate/surfactant pair).

These results take on their full meaning with regard to the prior art when it is realized that the quantity by dry weight of dispersant used according to the invention can be less than 1% of the total weight of dry talc.

DETAILED DESCRIPTION OF THE PREFERRED EMBODIMENTS

Thus, a first object of the invention is a method of manufacture of an aqueous suspension of talc, including a step of suspension in water of a talc, where the talc may result from a prior step of granulation, characterised in that at least one hydrosoluble polymer is used, during the step of suspension and/or during the step, if applicable, of granulation, characterised in that the hydrosoluble polymer comprises, consists essentially of, or consists of the following monomers in polymerized form:
- a) at least one (meth)acrylic monomer, and
- b) at least one monomer of formula (I):

R—(OE)$_m$-(OP)$_n$—R'      (I)

where
- m and n designate integers of less than or equal to 115, at least one of which is non-zero,
- OE and OP designate respectively ethylene oxide and propylene oxide, positioned in a regular or random manner,
- R designates a polymerizable group, chosen from among the acrylate, methacrylate, methacrylurethane, vinyl and allyl groups,
- R' designates hydrogen or a linear or branched alkyl group having fewer than 14 carbon atoms.

The (meth)acrylic monomer(s) in this hydrosoluble polymer include the (meth)acrylic monomer(s) of EP 0 892 020 A1, incorporated herein by reference.

Another object of the present invention is an aqueous suspension of talc in water, characterized in that it comprises at least one hydrosoluble polymer that comprises, consists essentially of, or consists of monomers a) and b) above in polymerized form.

Another object of the present invention lies in the use of the inventive aqueous suspension to manufacture a paper coating, an additive enabling the quantity of adhesives to be reduced, a paint, a plastic, a rubber, a ceramic, a food composition, a cosmetic composition, or an agricultural formulation.

Another object of the present invention is any one or more of a paper coating, an additive enabling the quantity of adhesives to be reduced, a paint, a plastic, a rubber, a ceramic, a food composition, a cosmetic composition or an agricultural formulation, that contains a talc and a hydrosoluble polymer as described above.

According to a preferred embodiment of the present invention, the objects above may also be characterized in that the hydrosoluble polymer comprises, consists essentially of, or consists of, expressed as a % by weight of each of its monomers:
- a) at least 60% of at least one (meth)acrylic monomer,
- b) at most 40% of at least one monomer of formula (I).

As used herein the term (meth)acrylic means methacrylic and acrylic, and supports both terms.

In a preferred embodiment of the present invention, in respect of the monomer of formula (I), when R' designates hydrogen, integers m and n are non-zero and preferably from 10-75.

In a preferred embodiment of the present invention, in respect of the monomer of formula (I), when R' designates a linear or branched alkyl group having fewer than 14 carbon atoms, integer n=0 and integer m is between 10 and 115.

According to another preferred embodiment of the present invention, the R' group of the monomer of formula (I) represents hydrogen.

According to another preferred embodiment, the hydrosoluble polymer comprises, consists essentially of, or consists of expressed as a % by weight of each of its monomers:
- a) of 60% to 99% of at least one (meth)acrylic monomer, and
- b) of 1% to 40% of a monomer of formula (I).

According to another preferred embodiment of the present invention, the hydrosoluble polymer has a specific viscosity of between 1 and 50, as measured according to the method described in document EP 0 892 020 A1.

The term "specific viscosity" in the meaning of the present invention is defined as the difference of the relative viscosity measured at a determined temperature (for example 20° C. or 25° C.) minus 1.

$$\eta_{sp} = \eta_{rel} - 1$$

The relative viscosity used here is the quotient of viscosity of solution $\eta$ and of the viscosity of solvent $\eta_0$ $$\eta_{rel} = \frac{\eta}{\eta_0}$$

where the viscosity of solvent $\eta_0$ is defined as the viscosity of the pure solvent at a determined temperature (for example 20° C. or 25° C.) and the viscosity of solution $\eta$ is defined as the viscosity of the comb copolymer dissolved in the pure solvent at a determined temperature (for example 20° C. or 25° C.) and at a determined polymer concentration (for example 45 g/l).

However, to determine the relative viscosity, it is sufficient to measure the elution time t (of the solution) and $t_0$ (of the solvent) at a given temperature (for example 20° C. or 25° C.) if the limit conditions are constant. Consequently, the relative viscosity can be defined by:

$$\eta_{rel} = \frac{t}{t_0}$$

and therefore the specific viscosity can be defined by:

$$\eta_{sp} = \frac{t}{t_0} - 1$$

The specific viscosity of the polymer can, for example, be determined by a Lauda PVS system, with aqueous polymer solutions (with a determined polymer concentration of 45 g/l or 50 g/l, for example). The measurements can notably be made on a type I Hubbelohde DIN (Schott) capillary tube (K=0.010).

According to another preferred embodiment of the present invention, the hydrosoluble polymer is totally or partially neutralised, preferentially by sodium, calcium, potassium, magnesium and ammonium ions or their blends.

According to another preferred embodiment of the present invention, the talc suspension in water contains between 0.001% and 2%, preferentially between 0.1% and 1%, and very preferentially between 0.1% and 0.75%, by dry weight of the hydrosoluble polymer relative to the dry weight of talc.

According to yet another preferred embodiment of the present invention, the suspension of talc in water contains more than 55%, preferentially more than 60%, and very preferentially between 61% and 65%, by dry weight of talc relative to its total weight.

EXAMPLES

Example 1

This example relates to the suspending of a talc which is Mistron 85 sold by the company Talc de Luzenac™.

In this case it was sought to achieve suspensions having a dry talc extract equal to 61% of their total weight.

Using the VMI Supertest™ (Rayneri™) motor a 61% dry extract talc dispersion was achieved.

In a stainless steel beaker the first step was to weigh the water required to have an end concentration of 61%. After this the polymer according to the invention or the polymer/CMC system or polymer/surfactant system to be tested was added (the quantities are given below, for each test).

The pH is adjusted to 12 with a 50% soda solution.

The talc is then poured into the beaker, little-by-little.

The motor stirring speed is then increased up to 2,500 revolutions/minute.

Stirring at this speed was continued for 20 minutes.

The suspension was allowed to cool until it reached 25° C.

The pH was again adjusted to 11 with a 50% soda solution.

For each of the suspensions obtained, in the second step the value of its Ford™ cup viscosity was determined using the method well known to the skilled man in the art (ISO 2431-1984 standard, using a no 4 Ford™ cup).

The presence of foam was assessed visually.

Test No 1:

This test illustrates the prior art, and more specifically a solution of the polyacrylate/CMC type, according to documents U.S. Pat. No. 6,267,811 A1 and WO 2010 055191 A1.

It uses, relative to the total weight of talc, 0.35% by dry weight of a sodium polyacrylate of average molecular mass by weight equal to 3,800 g/mole and 0.35% by dry weight of a CMC (Finnfix-5™ sold by the company CP-Kelko Oy™).

Test No 2:

This test illustrates the prior art and more specifically a variant of documents U.S. Pat. No. 6,267,811 A1 and WO 2010 055191 A1 based on a polyacrylate/surfactant pair.

It uses, relative to the total weight of talc, 0.1% by dry weight of a sodium polyacrylate of average molecular mass by weight equal to 3,800 g/mole and 0.9% by dry weight of a surfactant (Lumiten™ PR8709 sold by the company BASF™).

Test No 3:

This test illustrates the prior art, and more specifically a solution as described in document EP 0 892 020 A1, where the surfactant monomer is the carrier of a terminal hydrophobic group which is the linear alkyl group having 22 carbon atoms.

It uses, relative to the dry weight of talc, 0.5% by dry weight of a polymer (10% molar of the carboxylic sites of which are neutralised by the sodium ion) consisting of, expressed as a % by weight of each of its constituents:
  a) 79.5% of acrylic acid,
  b) 20.5% of a monomer of formula (I) with R designating the methacrylate group, n=0 and m=25, and R' is the linear alkyl group having 22 carbon atoms.

Test No 4:

This test illustrates the prior art, and more specifically a solution as described in document EP 0 892 020 A1, where the surfactant monomer is the carrier of a terminal hydrophobic group which is the aryl group having 30 carbon atoms, and where the group is tristyrylphenol.

It uses, relative to the dry weight of talc, 0.5% by dry weight of a polymer (10% molar of the carboxylic sites of which are neutralised by the sodium ion) consisting of, expressed as a % by weight of each of its constituents:
  a) 74.0% of acrylic acid,
  b) 26.0% of a monomer of formula (I) with R designating the methacrylurethane group, n=0 and m=40, and R' is the tristyrylphenol group having 30 carbon atoms.

Test No 5:

This test illustrates the prior art, and more specifically a solution as described in document EP 0 892 020 A1, where the surfactant monomer is the carrier of a terminal hydrophobic group which is the aryl group having 30 carbon atoms, and where the group is tristyrylphenol.

It uses, relative to the dry weight of talc, 0.5% by dry weight of a polymer (10% molar of the carboxylic sites of which are neutralised by the sodium ion) consisting of, expressed as a % by weight of each of its constituents:
a) 76.0% of acrylic acid,
b) 24.0% of a monomer of formula (I) with R designating the methacrylate group, n=0 and m=25, and R' is the tristyrylphenol group having 30 carbon atoms.

Test No 6:

This test illustrates a domain not belonging either to the invention or to the prior art; more specifically it illustrates a solution as described in document EP 0 892 020 A1, but with a surfactant monomer which is the carrier of a terminal hydrophobic group which is the linear alkyl group having 16 carbon atoms.

It uses, relative to the dry weight of talc, 0.5% by dry weight of a polymer (10% molar of the carboxylic sites of which are neutralised by the sodium ion) consisting of, expressed as a % by weight of each of its constituents:
a) 81.0% of acrylic acid,
b) 19.0% of a monomer of formula (I) with R designating the methacrylurethane group, n=0 and m=25, and R' is the linear alkyl group having 16 carbon atoms.

Test No 7:

This test illustrates the invention.

It uses, relative to the dry weight of talc, 0.5% by dry weight of a polymer (10% molar of the carboxylic sites of which are neutralised by the sodium ion) consisting of, expressed as a % by weight of each of its constituents:
a) 75.0% of acrylic acid,
b) 25.0% of a monomer of formula (I) with R designating the methacrylate group, n=40 and m=16, and R' is hydrogen.

Test No 8:

This test illustrates the invention.

It uses, relative to the dry weight of talc, 0.5% by dry weight of a polymer (10% molar of the carboxylic sites of which are neutralised by the sodium ion) consisting of, expressed as a % by weight of each of its constituents:
a) 70.0% of acrylic acid,
b) 30.0% of a monomer of formula (I) with R designating the methacrylate group, n=48 and m=16, and R' is hydrogen.

Test No 9:

This test illustrates the invention.

It uses, relative to the dry weight of talc, 0.5% by dry weight of a polymer (10% molar of the carboxylic sites of which are neutralised by the sodium ion) consisting of, expressed as a % by weight of each of its constituents:
a) 65.0% of acrylic acid,
b) 35.0% of a monomer of formula (I) with R designating the methacrylate group, n=48 and m=16, and R' is hydrogen.

Test No 10:

This test illustrates the invention.

It uses, relative to the dry weight of talc, 0.5% by dry weight of a polymer (10% molar of the carboxylic sites of which are neutralised by the sodium ion) consisting of, expressed as a % by weight of each of its constituents:
a) 60.0% of acrylic acid,
b) 40.0% of a monomer of formula (I) with R designating the methacrylate group, n=48 and m=16, and R' is hydrogen.

Test No 11:

This test illustrates the invention.

It uses, relative to the dry weight of talc, 0.5% by dry weight of a polymer (10% molar of the carboxylic sites of which are neutralised by the sodium ion) consisting of, expressed as a % by weight of each of its constituents:
a) 77.0% of acrylic acid,
b) 23.0% of a monomer of formula (I) with R designating the methacrylate group, n=0 and m=45, and R' is the methyl group.

Test No 12:

This test illustrates the invention.

It uses, relative to the dry weight of talc, 0.5% by dry weight of a polymer (50% molar of the carboxylic sites of which are neutralised by the potassium ion) consisting of, expressed as a % by weight of each of its constituents:
a) 77.0% of acrylic acid,
b) 23.0% of a monomer of formula (I) with R designating the methacrylate group, n=0 and m=113, and R' is the methyl group.

TABLE 1

| Test n° | 1 | 2 | 3 | 4 | 5 |
|---|---|---|---|---|---|
| Reference (R) | R | R | R | R | R |
| Invention (IN) | | | | | |
| Outside scope of Invention (HI) | | | | | |
| Additive* | polyacrylate CMC | polyacrylate surfactant | polymer surfactant | polymer surfactant | polymer surfactant |
| R' | — | — | alkyl C22 | TSP C30 | TSP C30 |
| Ford ™ cup viscosity (s) | 253 | 80** | 286 | 171 | 124 |

| Test n° | 6 | 7 | 8 | 9 | 10 |
|---|---|---|---|---|---|
| Reference (R) | | | | | |
| Invention (IN) | HI | IN | IN | IN | IN |
| Outside scope of Invention (HI) | | | | | |
| additive | polymer surfactant | polymer surfactant | polymer surfactant | polymer surfactant | polymer surfactant |

TABLE 1-continued

| R' | alkyl C16 | H | H | H | H |
|---|---|---|---|---|---|
| Ford™ cup viscosity (s) | 131 | 98 | 92 | 75 | 97 |

| Test n° | 11 | 12 |
|---|---|---|
| Reference (R) Invention (IN) Outside scope of Invention (HI) | IN | IN |
| additive | polymer surfactant | polymer surfactant |
| R' | alkyl C1 | alkyl C1 |
| Ford™ cup viscosity (s) | 90 | 110 |

*additive designates the system used to disperse (and stabilise the suspension) based on a polyacrylate/CMC or polyacrylate/surfactant pair or a surfactant polymer
**presence of very abundant foam A reading of Table 1 demonstrates that the polyacrylate/surfactant system according to test no 1 is genuinely inefficient: it leads to the high Ford™ cup viscosity.

Conversely, the polyacrylate/surfactant pair of test no 2 could constitute an advantageous solution, since it is associated with a Ford™ cup viscosity value of only 80 seconds. However, the formation of an extremely abundant foam is very clearly observed. And such a foam is completely incompatible with the use of the suspension to manufacture an end product, such as a paint, a paper coating, etc. It must be added that none of the other 11 tests led to the formation of foam.

Tests no 3, 4 and 5, which use a polymer the surfactant monomer of which has more than 22 carbon atoms in its terminal group, systematically lead to higher Ford™ cup viscosity values (over 120 seconds) than for the polymers of the invention (less than 110 seconds).

Finally, test no 6, which illustrates the presence of an alkyl group having 16 carbon atoms in the surfactant monomer, leads to a Ford™ cup viscosity value equal to 131, which is also not satisfactory.

To summarise, only the polymers according to the invention (tests no 7 to 12) lead both to the lowest Ford™ cup viscosity values (less than 110 seconds), without causing the formation of foam, and with a low dose of dispersant.

Example 2

This example relates to the suspending of a talc purified by flotation which is Finntalc™ C10 sold by the company Mondo Minerals™.

This example illustrates the capacity of the dispersant according to the invention to suspend another type of talc than the previous one: it is used to illustrate the "universal" character of the dispersant.

In this case it was sought to achieve suspensions having a dry talc extract equal to 65% of their total weight.

In a stainless steel beaker, the water required to have an end concentration of 68% by dry weight of talc in the water was weighed.

After this the polymer or the polymer/CMC system or polymer/surfactant system to be tested was added (the quantities are given below, for each test).

The pH of the solution is adjusted to 12 by means of a 50% soda solution.

The aqueous solution is introduced into a Lödige mixer; after the mixer is started the talc is introduced little-by-little into it. The turbine which provides high shearing is then started, and is left to operate for 1 hour, regulating the temperature of the suspension to between 30 and 40° C.

The suspension is then diluted to a dry extract of 65% talc. Its pH is adjusted to 10 by means of a 50% soda solution.

For each of the suspensions obtained, in the second step the value of its Ford™ cup viscosity was determined using the method well known to the skilled man in the art (ISO 2431-1984 standard, using a no 4 Ford™ cup).

The presence of foam was assessed visually.

Test No 13:

This test illustrates the prior art, and more specifically a solution of the polyacrylate/CMC type, according to documents U.S. Pat. No. 6,267,811 A1 and WO 2010 055191 A1.

It uses, relative to the total weight of talc, 0.35% by dry weight of a sodium polyacrylate of average molecular mass by weight equal to 3,800 g/mole and 0.35% by dry weight of a CMC (Finnfix-5™ sold by the company CP-Kelko Oy™). For this test it is necessary to begin to disperse with a 65% dry extract, and then to dilute to an end dry extract of 61% by dry weight of talc, without which it is impossible to obtain a handleable suspension.

Test No 14:

This test illustrates the prior art and more specifically a variant of documents U.S. Pat. No. 6,267,811 A1 and WO 2010 055191 A1 based on a polyacrylate/surfactant pair.

It uses, relative to the total weight of talc, 0.15% by dry weight of a sodium polyacrylate of average molecular mass by weight equal to 3,800 g/mole and 1.5% by dry weight of a surfactant (Lumiten™ PR8709 sold by the company BASF™).

Test No 15:

This test illustrates the invention.

It uses, relative to the dry weight of talc, 0.6% by dry weight of a polymer (50% molar of the carboxylic sites of which are neutralised by the sodium ion) consisting of, expressed as a % by weight of each of its constituents:

a) 65.0% of acrylic acid,
b) 35.0% of a monomer of formula (I) with R designating the methacrylate group, n=48 and m=16, and R' is hydrogen.

Test No 16:

This test illustrates the invention.

It uses, relative to the dry weight of talc, 0.6% by dry weight of a polymer (50% molar of the carboxylic sites of which are neutralised by the sodium ion) consisting of, expressed as a % by weight of each of its constituents:

a) 77.0% of acrylic acid,
b) 23.0% of a monomer of formula (I) with R designating the methacrylate group, n=0 and m=45, and R' is the methyl group.

TABLE 2

| Test n° | 13 | 14 | 15 | 16 |
|---|---|---|---|---|
| Reference (R) Invention (IN) | R | R | IN | IN |
| Additive* | polyacrylate CMC | polyacrylate surfactant | polymer surfactant | polymer surfactant |
| R' | — | — | H | alkyl C1 |
| Ford™ cup viscosity (s) | 305 | 100** | 95 | 105 |

*additive designates the system used to disperse (and stabilise the suspension) based on a polyacrylate/CMC or polyacrylate/surfactant pair or a surfactant polymer
**very abundant foam A reading of table 2 demonstrates that the polyacrylate/CMC system according to test no 13 is genuinely inefficient: it leads to the highest Ford™ cup viscosity.

Conversely, the polyacrylate/surfactant pair according to test no 14 could constitute an advantageous solution (however, it should be noted that the dose by dry weight of additives used is in this case equal to 1.65% of the dry weight of talc, compared to only 0.6% of polymer of the invention). In addition, the formation of an extremely abundant foam is very clearly observed. None of the other tests caused foam.

Tests no 15 and 16, which are tests with a polymer according to the invention, lead to some of the lowest Ford™ cup values, without causing the formation of foam, and with a low dispersant dose.

A listing of highly preferred embodiments appears below:

1—A method of preparing an aqueous suspension of talc, comprising:
optionally granulating talc; and
suspending said talc in water,
wherein at least one of said granulating and suspending take place in the presence of at least one hydrosoluble polymer comprising:
a) at least one (meth)acrylic monomer, and
b) at least one monomer of formula (I):

$$R\text{—}(OE)_m\text{-}(OP)_n\text{—}R' \qquad (I)$$

where
m and n independently designate integers of less than or equal to 115, at least one of which is non-zero,
OE and OP designate respectively ethylene oxide and propylene oxide,
R designates a polymerisable group, chosen from among the acrylate, methacrylate, methacrylurethane, vinyl or allyl groups, and
R' designates hydrogen or a linear or branched alkyl group having fewer than 14 carbon atoms.

2—A method according to Embodiment 1, wherein the R' represents hydrogen.

3—A method according to Embodiment 1, wherein the hydrosoluble polymer consists, expressed as a % by weight of each of its monomers, of:
a) at least 60% of said at least one (meth)acrylic monomer,
b) at most 40% of said at least one monomer of formula (I).

4—A method according to Embodiment 1, wherein the hydrosoluble polymer consists, expressed as a % by weight of each of its monomers, of:
a) 60% to 99% of said at least one (meth)acrylic monomer, and
b) 1% to 40% of said monomer of formula (I).

5—A method according to Embodiment 1, wherein R' is hydrogen and integers m and n independently are any integer from 10-75.

6—A method according to Embodiment 1, wherein R' is a linear or branched alkyl group having fewer than 14 carbon atoms, n=0 and m is any integer from 10-115.

7—A method according to Embodiment 1, wherein the hydrosoluble polymer has a specific viscosity of between 1 and 50.

8—A method according to Embodiment 1, wherein the hydrosoluble polymer is totally or partially neutralized.

9—A method according to Embodiment 1, wherein the aqueous suspension of talc comprises from 0.001%-2% by dry weight of the hydrosoluble polymer relative to the dry weight of talc.

10—A method according to Embodiment 1, wherein the aqueous suspension of talc comprises more than 55% by dry weight of talc relative to its total weight.

11—An aqueous suspension of talc in water, comprising talc, water, and at least one hydrosoluble polymer comprising:
a) at least one (meth)acrylic monomer, and
b) at least one monomer of formula (I):

$$R\text{—}(OE)_m\text{-}(OP)_n\text{—}R' \qquad (I)$$

where
m and n independently designate integers of less than or equal to 115, at least one of which is non-zero,
OE and OP designate respectively ethylene oxide and propylene oxide,
R designates a polymerisable group, chosen from among the acrylate, methacrylate, methacrylurethane, vinyl or allyl groups, and
R' designates hydrogen or a linear or branched alkyl group having fewer than 14 carbon atoms.

12—An aqueous suspension of talc in water according to Embodiment 11, wherein R' represents hydrogen.

13—An aqueous suspension of talc in water according to Embodiment 11, wherein the hydrosoluble polymer consists, expressed as a % by weight of each of its monomers:
a) at least 60% of said at least one (meth)acrylic monomer, and
b) at most 40% of said at least one monomer of formula (I).

14—An aqueous suspension of talc in water according to Embodiment 11, wherein the hydrosoluble polymer consists, expressed as a % by weight of each of its monomers:
a) of 60% to 99% of said at least one (meth)acrylic monomer, and
b) of 1% to 40% of said at least one monomer of formula (I).

15—An aqueous suspension of talc in water according to Embodiment 11, wherein R' is hydrogen and m and n are independently any integer from 10 to 75.

16—An aqueous suspension of talc in water according to Embodiment 11, wherein R' is a linear or branched alkyl group having fewer than 14 carbon atoms, n=0 and m is any integer from 10 to 115.

17—An aqueous suspension of talc in water according to Embodiment 11, wherein the hydrosoluble polymer has a specific viscosity of between 1 and 50.

18—An aqueous suspension of talc in water according to Embodiment 11, wherein the hydrosoluble polymer is totally or partially neutralized.

19—An aqueous suspension of talc in water according to Embodiment 11, comprising 0.001%-2% by dry weight of the hydrosoluble polymer relative to the dry weight of talc.

20—An aqueous suspension of talc in water according to Embodiment 11, comprising more than 55% by dry weight of talc relative to its total weight.

21—A composition comprising talc and a hydrosoluble polymer, wherein said hydrosoluble polymer comprises:

a) at least one (meth)acrylic monomer, and
b) at least one monomer of formula (I):

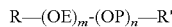  (I)

where m and n independently designate integers of less than or equal to 115, at least one of which is non-zero, OE and OP designate respectively ethylene oxide and propylene oxide, R designates a polymerisable group, chosen from among the acrylate, methacrylate, methacrylurethane, vinyl or allyl groups, and R' designates hydrogen or a linear or branched alkyl group having fewer than 14 carbon atoms.

22—A composition according to Embodiment 21, where said composition is a paper coating, an additive enabling the quantity of adhesives to be reduced, a paint, a plastic, a rubber, a ceramic, a food formulation, a cosmetic formulation, or an agricultural formulation.

23—A method, comprising coating paper with the composition according to Embodiment 22.

When a polymer is referred to herein as including, containing, comprising, etc. a monomer, those of ordinary skill understand that this is a shorthand convenience, and that the monomer is present in the polymer in polymerized form.

As used herein the terms composed of, contains, containing, and terms similar thereto, when referring to the ingredients, parts, reactants, etc., of a composition, component, etc., mean, in their broadest sense, "includes at least" (i.e., comprises) but also include within their definition all those gradually restricted meanings until and including the point where only the enumerated materials are included (e.g., consisting essentially of and consisting of).

As used herein, the phrases "selected from the group consisting of," "chosen from," and the like include mixtures of the specified materials. The term "mentioned" notes exemplary embodiments, and is not limiting to certain species. As used herein the words "a" and "an" and the like carry the meaning of "one or more."

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The above written description of the invention provides a manner and process of making and using it such that any person skilled in this art is enabled to make and use the same, this enablement being provided in particular for the subject matter of the appended claims, which make up a part of the original description.

The invention claimed is:

1. A method of preparing an aqueous suspension of talc, comprising:

granulating talc; and
suspending said granulated talc in water,
wherein at least one of said granulating and suspending take place in the presence of an anionic hydrosoluble polymer, said anionic hydrosoluble polymer consisting, expressed as a % by weight of each of its monomers, of at least 60% of at least one (meth)acrylic acid monomer and at most 40% of at least one monomer of formula (I):

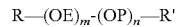  (I)

where m and n independently designate integers of less than or equal to 115, at least one of which is non-zero, OE and OP designate respectively ethylene oxide and propylene oxide, R designates a polymerizable group, chosen from acrylate, methacrylate, methacrylurethane, vinyl and allyl groups, and R' designates hydrogen, and wherein the aqueous suspension of talc prepared comprises more than 55% by dry weight of talc relative to its total weight.

2. A method according to claim 1, wherein the hydrosoluble polymer consists, expressed as a % by weight of each of its monomers, of 60% to 99% of said at least one (meth)acrylic acid monomer and 1% to 40% of said monomer of formula (I).

3. A method according to claim 1, wherein integers m and n independently are any integer from 10-75.

4. A method according to claim 1, wherein the hydrosoluble polymer has a specific viscosity of between 1 and 50.

5. A method according to claim 1, wherein the hydrosoluble polymer is totally or partially neutralized.

6. A method according to claim 1, wherein the aqueous suspension of talc comprises from 0.001%-2% by dry weight of the hydrosoluble polymer relative to the dry weight of talc.

7. A method according to claim 1, wherein the aqueous suspension of talc comprises 61%-65% by dry weight of said talc relative to its total weight.

8. An aqueous suspension of talc in water, comprising more than 55% by dry weight of talc relative to its total weight, water, and at least one anionic hydrosoluble polymer consisting, expressed as a % by weight of each of its monomers, of 60% to 99% of at least one (meth)acrylic acid monomer and 1% to 40% of at least one monomer of formula (I):

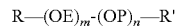  (I)

where m and n independently designate integers of less than or equal to 115, at least one of which is non-zero, OE and OP designate respectively ethylene oxide and propylene oxide, R designates a polymerisable group, chosen from among the acrylate, methacrylate, methacrylurethane, vinyl or allyl groups, and R' designates hydrogen.

9. An aqueous suspension of talc in water according to claim 8, wherein m and n are independently any integer from 10 to 75.

10. An aqueous suspension of talc in water according to claim 8, wherein the hydrosoluble polymer has a specific viscosity of between 1 and 50.

11. An aqueous suspension of talc in water according to claim 8, wherein the hydrosoluble polymer is totally or partially neutralized.

12. An aqueous suspension of talc in water according to claim 8, comprising 0.001%-2% by dry weight of the hydrosoluble polymer relative to the dry weight of talc.

13. A method according to claim 1, wherein said granulating talc takes place in the presence of said hydrosoluble polymer.

14. A method according to claim 1, wherein said suspending takes place in the presence of said hydrosoluble polymer.

15. A method according to claim 13, wherein said suspending takes place in the presence of said hydrosoluble polymer.

* * * * *